United States Patent
Sun

(10) Patent No.: US 8,617,448 B2
(45) Date of Patent: Dec. 31, 2013

(54) METHODS OF MAKING AN ENDOVASCULAR PROSTHESIS USING A DEFORMABLE MATRIX

(75) Inventor: Jichao Sun, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 744 days.

(21) Appl. No.: 12/598,249

(22) PCT Filed: May 19, 2008

(86) PCT No.: PCT/US2008/006430
§ 371 (c)(1),
(2), (4) Date: May 12, 2010

(87) PCT Pub. No.: WO2008/144053
PCT Pub. Date: Nov. 27, 2008

(65) Prior Publication Data
US 2010/0219562 A1   Sep. 2, 2010

Related U.S. Application Data

(60) Provisional application No. 60/930,761, filed on May 17, 2007.

(51) Int. Cl.
*B28B 7/30* (2006.01)

(52) U.S. Cl.
USPC ........... 264/313; 264/317; 264/221; 425/440; 249/61; 249/62; 249/183

(58) Field of Classification Search
USPC ............. 264/313, 317, 221; 425/440; 249/61, 249/62, 183
See application file for complete search history.

(56) References Cited

U.S. PATENT DOCUMENTS

| | | | |
|---|---|---|---|
| 3,953,566 A | 4/1976 | Gore | 264/288 |
| 4,110,396 A * | 8/1978 | Reynolds | 264/236 |
| 4,675,361 A | 6/1987 | Ward, Jr. | 525/92 |
| 4,861,830 A | 8/1989 | Ward, Jr. | 525/92 |
| 5,017,664 A | 5/1991 | Grasel et al. | 525/454 |
| 5,589,563 A | 12/1996 | Ward et al. | 528/44 |
| 5,599,352 A * | 2/1997 | Dinh et al. | 128/898 |
| 5,980,799 A | 11/1999 | Martakos et al. | 264/127 |
| 6,203,732 B1 * | 3/2001 | Clubb et al. | 264/313 |
| 6,547,815 B2 | 4/2003 | Myers | 623/1.13 |
| 6,605,119 B1 | 8/2003 | Colone et al. | 623/901 |
| 6,929,663 B2 * | 8/2005 | Rioux et al. | 623/23.64 |

(Continued)

FOREIGN PATENT DOCUMENTS

WO   WO 00/18328 A1   4/2000

OTHER PUBLICATIONS

Callister, Materials Science and Engineering an Introduction, 2007, Wiley, 7th Edition, pp. 137-140, 143, 144, G3, G4, and G9.*

(Continued)

*Primary Examiner* — Timothy Kennedy
(74) *Attorney, Agent, or Firm* — Brinks Gilson & Lione

(57) ABSTRACT

A method of making an endovascular prosthesis comprises the steps of applying a first layer of polymer to a portion of a deformable matrix, contacting a stent with the polymer to deform the matrix, applying a second layer of polymer over at least a portion of the stent and first layer, solidifying the layers of polymer to form the endovascular prosthesis, and removing the matrix.

17 Claims, 4 Drawing Sheets

(56) References Cited

U.S. PATENT DOCUMENTS

| | | | |
|---|---|---|---|
| 6,939,377 B2 | 9/2005 | Jayaraman et al. | 623/1.46 |
| 2001/0010012 A1* | 7/2001 | Edwin et al. | 623/1.13 |
| 2002/0187288 A1 | 12/2002 | Lim et al. | 428/35.2 |
| 2003/0060871 A1 | 3/2003 | Hill et al. | 623/1.15 |
| 2004/0068249 A1* | 4/2004 | Kampa et al. | 604/523 |

OTHER PUBLICATIONS

International Search Report for related International application No. PCT/US2008/006430, dated Jul. 3, 2009, 3 pgs.

* cited by examiner

METHODS OF MAKING AN ENDOVASCULAR PROSTHESIS USING A DEFORMABLE MATRIX

CROSS-REFERENCE TO RELATED APPLICATION

This application claims the benefit under 35 U.S.C. §371 of International Application No. PCT/US2008/006430, filed May 19, 2008, which claims the benefit of U.S. Provisional Patent Application Ser. No. 60/930,761, filed May 17, 2007, which are incorporated herein by reference.

BACKGROUND

1. Technical Field

This invention relates to methods of manufacturing endovascular prostheses using a deformable matrix.

2. Background Information

The functional vessels of human and animal bodies, such as blood vessels and ducts, occasionally weaken or even rupture. For example, in the aortic artery, the vascular wall can weaken, resulting in dangerous conditions such as aneurysms and dissections. Upon further exposure to hemodynamic forces, such an aneurysm can rupture.

One treatment for aneurysms includes using stent grafts that include one or more stents affixed to a graft material. The stent grafts are placed within vascular networks and are secured at the treatment site by endovascular insertion using inducers and catheters. They are then enlarged radially and remain in place by attachment to the vessel wall. In particular, stent grafts are used to treat descending thoracic and abdominal aortic aneurysms. At one end the stent graft defines a single lumen for placement within the aorta and a distal end is bifurcated to define two lumens extending into the branch arteries. It is important to effectively exclude an aneurysm by providing a seal both proximally and distally to the aneurysm such that a patient's blood flow is shunted through the stent graft and not the diseased vasculature. A device of this type can, for example, treat various arterial aneurysms, including those in the thoracic aorta, abdominal aorta, iliac, or hypogastric artery.

Stent grafts are susceptible to certain latent complications, such as instability leading to kinking, obstruction of the lumen and/or disintegration leading to possible graft explanation. For instance, the stent graft may become displaced from its intended position due to larger displacement forces within the smaller diameter stent graft portions. Stent grafts are also susceptible to different types of endoleaks. In some cases, the endoleaks cause a relapse of the conditions the stent grafts were employed to treat. Endoleaks are sometimes caused or aggravated by graft migration in addition to other factors.

Two closely related aspects of stent graft function, therefore, are sealing and fixation. A stent graft often engages the wall of a lumen on both ends of the aneurysm or other defect at proximal and distal regions referred to as landing or sealing zones. Typically these sealing zones are located near the termini of the stent grafts. The seal between the stent graft and the vascular wall is typically formed at these locations as a result of the circumferential apposition of the stent graft to the vascular wall. This apposition is usually maintained by the radial force exerted by the stents attached to the stent graft.

The term "stent graft" refers to a type of endovascular prosthesis made of a tubular graft material and supported by at least one stent.

The major functional requirements of a covered stent include the usual vasculature support functions typical of a bare stent and the addition of a barrier which may exclude an aneurysm or simply be used to trap plaque against the vascular wall (e.g., as in the case of a carotid stent application). In both cases, it would be desirable for the barrier element to completely cover the perimeter of the stent surface. A secure attachment between the covering and the stent is important because delamination leads to separation of the covering from the stent. This delamination negates the stent graft's effectiveness as a covered stent. Delamination also may lead to "flaps" that may partially occlude the lumen and lead to local turbulent blood flow. This often results in localized or focal stenosis and, possibly, to complete occlusion. Small diameter (e.g., 8 mm) stents are very susceptible to this complication. Larger diameter (e.g., 28 mm) stents are capable of mitigating the localized hemodynamic turbulence.

Complicating the issue is the relatively small diameter (e.g., 8 mm) as compared to endovascular stent-grafts where their large diameters (e.g., 28 mm) mitigate the localized hemodynamic turbulence.

The stent and the graft material of endovascular prostheses are often attached using hand-sewn sutures. This method of attachment is highly skilled, labor-intensive, time-consuming, and expensive.

Another method of attaching the stent and the graft material of an endoluminal prosthesis together is to cover the stent with an adhesive or a polymer coating that will allow the stent to be bonded to the graft material. Unfortunately, this type of attachment has several drawbacks. For example, this technique often requires multiple steps, since the stent must be treated with the adhesive or polymer coating before the process of attaching the graft can begin. Furthermore, the process of coating the stent with the adhesive or polymer coating usually requires multiple steps. Typically, the adhesive or coating is applied in a first step, using a variety of methods, and then must be cured in a subsequent step. In addition, once the adhesive or polymer coating has been applied to the stent and the graft material has been placed over or within the coated stent, actual bonding between the graft material and the adhesive or the polymer coating usually requires heating the coated stent and the graft material in an oven or other heating device. Unfortunately, this heating process limits the types of graft materials that can be used and may also affect the integrity of the graft material itself. In addition, this heating process can also thermoplastically fuse large portions of the graft material.

Current manufacturing methods for polymer covered stents use rigid mandrels made of glass or stainless steel. Several layers of polymer are first added onto a glass or stainless steel mandrel. Then a stent is placed over the polymer and mandrel before several more layers of polymer on added to the albumen.

When polymers are used as coatings in methods using rigid mandrels at times, the polymer layer does not maintain an even coat over the stent graft at times. As a result, the layer may not completely encapsulate the stent graft. If a rigid mandrel is used, intimate contact between the stent outer surface and the covering polymer requires precise sizing. If the stent is too small, it may stick on the mandrel and destroy the covering during the process of extracting it from the mandrel. If it is too large, the covering may simply not encapsulate the stent.

BRIEF SUMMARY

In one embodiment, the present invention provides a method of making an endovascular prosthesis having a desired shape using a deformable matrix. A first layer of polymer is applied to a portion of the deformable matrix by means known in the art. A stent contacts the polymer to deform the matrix. A second layer of polymer is applied over at least a portion of the stent and first layer. The layers of polymer are solidified using methods known in the art to thereby form the endovascular prosthesis. The deformable matrix is removed from contact with the endovascular prosthesis. In some embodiments, the deformable matrix is removed after the polymer has been cured and the prosthesis has been formed.

In another aspect of the invention, the deformable matrix is removed from the prosthesis by a physical change or chemical change. The matrix can be comprised of wax, polymer, or elastomer, for instance, so that it may be removed without substantially damaging the formed prosthesis. In some embodiments, the matrix can be a mandrel or mold. The physical change can be accomplished through melting or constricting the diameter of the matrix. The matrix can also be dissolved by solvent, for instance.

In yet another aspect of the invention, the stent is pressed into the polymer coated matrix to decrease the amount of exposed surface area of the stent. In some embodiments where the matrix is a mandrel, the stent can be pressed into the outer surface of the mandrel, the outer surface having already been coated with polymer. There are embodiments where the stent is fixed around the mandrel and the diameter of the mandrel is enlarged to contact the stent. The matrix can be a mold having an inner lumen along which polymer can be covered. A stent can be placed along the inner lumen and pressed into the matrix, by a balloon catheter, for example.

There is also a method comprising applying a first layer of polymer to a portion of a deformable matrix. A graft material is applied over a portion of the deformable matrix. The graft material also contacts a stent to deform the matrix. A second layer of polymer is applied over at least a portion of the stent and graft material. The deformable matrix is removed from contact with the endovascular prosthesis.

In yet another embodiment of the present invention, the deformable matrix can be manipulated to a desired shape after the stent and/or graft material has been applied to the matrix and before curing the polymer. The desired shape is suitable for placement in a diseased vasculature.

DETAILED DESCRIPTION OF THE DRAWINGS AND THE PRESENTLY PREFERRED EMBODIMENTS

Figure 1A:
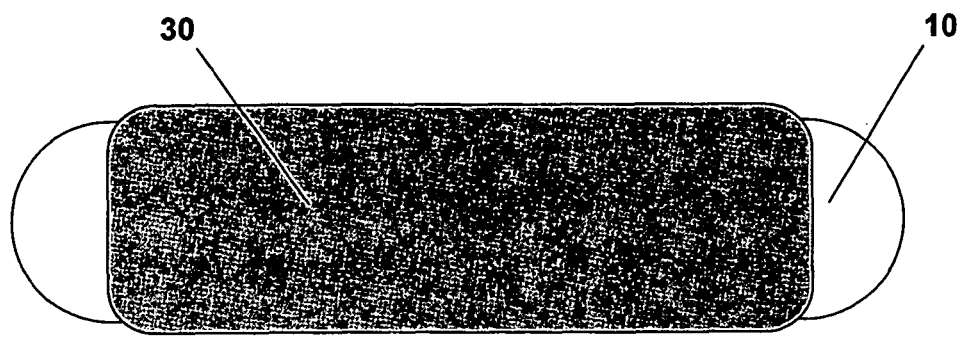
FIG. 1A is an exemplary illustration of a mandrel covered with a polymer.

Unless defined otherwise, all technical and scientific terms used herein have the same meaning as commonly understood to one of ordinary skill in the art to which this invention belongs.

The term "graft or graft material" means a generally cannular or tubular member which acts as an artificial vessel or prosthesis. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto the mandrel of the present invention. Preferably, polymers of the present invention, although added in layers onto the mandrel, after curing, result in one layer that encapsulates a stent or woven graft. This also aids in decreasing the incidence of delamination of the resulting endovascular prosthesis.

The graft material is a biocompatible material that is both flexible and abrasion resistant. Furthermore, the graft material should be selected from those materials that are particularly well suited for thermoplastic deformation, such that the material can be thermoplastically fused to a stent. Preferably, the graft material is a woven polyester. More preferably, the graft material is a polyethylene terephthalate (PET), such as DACRON® (DUPONT, Wilmington, Del.) or TWILL-WEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

In another embodiment, the woven graft material may be made of a single material, or it may be a blend, weave, laminate, or composite of two or more materials. The graft material may also include other additives, such as plasticizers, compatibilizers, surface modifiers, biological materials such as peptides and enzymes, and therapeutic agents such as drugs or other pharmaceutically effective medicaments. The therapeutic agents can comprise agents, or combinations thereof, that can affect the cells in a vessel wall, including drugs, chromophores, and nucleic acids. Therapeutic agents also comprise diagnostics such as radiopaque compounds that allow the vessel to be visualized by fluoroscopy or like methods. Therapeutic agents can also comprise antimicrobial agents, such as antibacterial and antiviral agents.

More preferably, the graft includes a biocompatible polyurethane. Examples of biocompatible polyurethanes include Thoralon® (THORATEC, Pleasanton, Calif.), BIOSPAN®, BIONATE®, ELASTHANE®, PURSIL®, and CARBO-SIL® (POLYMER TECHNOLOGY GROUP, Berkeley, Calif.).

Most preferably, the polymer graft contains the polyurethane Thoralon®. As described in U.S. Pat. No. 6,939,377, incorporated herein by reference, Thoralon® is a polyetherurethane urea blended with a siloxane-containing surface modifying additive. Specifically, the polymer is a mixture of base polymer BPS-215 and an additive SMA-300. The concentration of additive may be in the range of 0.5% to 5% by weight of the base polymer. The BPS-215 component (THORATEC) is a segmented polyether urethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). The SMA-300 component (THORATEC) is a polyurethane comprising polydimethylsiloxane as a soft segment and the reaction product of MDI and 1,4-butanediol as a hard segment. A process for synthesizing SMA-300 is described, for example, in U.S. Pat. Nos. 4,861,830 and 4,675,361, which are incorporated herein by reference. A polymer graft material can be formed from these two components by dissolving the base polymer and additive in a solvent such as dimethylacetamide (DMAC) and solidifying the mixture by solvent casting or by coagulation in a liquid that is a non-solvent for the base polymer and additive.

Polymers coated onto the mandrel can comprise polyurethane, such as Thoralon®. Thoralon® has been used in certain vascular applications and is characterized by thromboresistance, high tensile strength, low water absorption, low critical surface tension, and good flex life. Thoralon® is believed to be biostable and to be useful in vivo in long term blood contacting applications requiring biostability and leak resistance. Because of its flexibility, Thoralon® is useful in larger vessels, such as the abdominal aorta, where elasticity and compliance is beneficial.

In addition to Thoralon, other polyurethane ureas may be used as the graft material. For example, the BPS-215 component with a MDI/PTMO mole ratio ranging from about 1.0 to about 2.5 may be used.

In addition to polyurethane ureas, other polyurethanes, preferably those having a chain extended with diols, may be used as the graft material. Polyurethanes modified with cationic, anionic, and aliphatic side chains may also be used. See, for example, U.S. Pat. No. 5,017,664. Polyurethanes may need to be dissolved in solvents such as dimethyl formamide, tetrahydrofuran, dimethyacetamide, dimethyl sulfoxide, or mixtures thereof.

In addition, the polyurethanes may also be end-capped with surface active end groups, such as, for example, polydimethylsiloxane, fluoropolymers, polyolefin, polyethylene oxide, or other suitable groups. See, for example, the surface active end groups disclosed in U.S. Pat. No. 5,589,563, which is incorporated herein by reference.

In one embodiment, the graft material may contain a polyurethane having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. Examples of siloxane-polyurethanes are disclosed in U.S. Pat. Pub. No. 2002/0187288 A1, which is incorporated herein by reference.

The graft may contain polytetrafluoroethylene or expanded polytetratfluoroethylene (ePTFE). The structure of ePTFE can be characterized as containing nodes connected by fibrils. The structure of ePTFE is disclosed, for example, in U.S. Pat. Nos. 6,547,815 B2; 5,980,799; and 3,953,566; all of which are incorporated herein by reference.

If so desired, the polymers described above can be processed to form porous polymer grafts using standard processing methods including solvent-based processes such as casting, spraying, and dipping and melt extrusion processes. Extractable pore forming agents can be used during processing to produce porous polymer graft material. Examples of the particulate used to form the pores include a salt, including, but not limited to, sodium chloride (NaCl), sodium bicarbonate ($NaHCO_3$), $Na_2CO_3$, $MgCl_2$, $CaCO_3$, calcium fluoride ($CaF_2$), magnesium sulfate ($MgSO_4$), $CaCl_2$, $AgNO_3$, or any water soluble salt. However, other suspended particulate materials may be used. These include, but are not limited to, sugars, polyvinyl alcohol, cellulose, gelatin, or polyvinyl pyrolidone. Preferably, the particulate is sodium chloride; more preferably, the particulate is a sugar.

Therapeutic agents can be incorporated into the graft material of the prosthesis, or into the biocompatible coating which encapsulates the stent, so that they can be released into the body surrounding the lumen wall upon expansion and curing of the prosthesis. Therapeutic agents or medicaments can be impregnated into the lumen wall by pressure from expansion of the prosthesis. The therapeutic agent can also be photoreleasably linked to the surface of the prosthesis so that, upon contact with the surrounding lumen wall, the agent is released onto the cells of the adjacent vascular wall by exposure to radiation delivered via an optical fiber.

The term "stent" means any device that provides rigidity, expansion force, or support to a prosthesis, such as a stent graft. In one configuration, the stent may represent a plurality of discontinuous devices. In another configuration, the stent may represent one device. The stent may be located on the exterior of the device, the interior of the device, or both. Stents may have a wide variety of configurations and may be balloon-expandable or self-expanding. Typically, stents have a circular cross-section when fully expanded, so as to conform to the generally circular cross-section of a body lumen. In one example, a stent may comprise struts and acute bends or apices that are arranged in a zig-zag configuration in which the struts are set at angles to each other and are connected by the acute bends. The stent struts may have a thickness ranging from about 0.060 mm to about 0.20 mm and all combinations and subcombinations therein.

Preferably, the stent is formed from nitinol, stainless steel, tantalum, titanium, gold, platinum, inconel, iridium, silver, tungsten, cobalt, chromium, or another biocompatible metal, or alloys of any of these. Examples of other materials that may be used to form stents include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof; a polyanhydride, polycaprolactone, polyhydroxybutyrate valerate or another biodegradable polymer, or mixtures or copolymers of these; a protein, an extracellular matrix component, collagen, fibrin, or another biologic agent; or a suitable mixture of any of these. Preferably, the stent is a nitinol or stainless steel stent.

Generally, this invention provides methods of making an endovascular prosthesis using a deformable matrix or substrate to substantially prevent later delamination of the prosthesis. The method comprises applying polymer to a portion of a deformable matrix and placing a stent over the polymer coated deformable matrix. A second layer of polymer is added and the matrix is removed by either a physical or chemical change. In an embodiment that may be preferred, the method comprises applying a first layer of polymer onto a portion of a deformable matrix. The polymer is contacted by a stent to deform the matrix. A second layer of polymer is applied over at least a portion of the stent and first layer. The polymer layers are solidified to thereby form the endovascular prosthesis. The matrix is removed from contact with the endovascular prosthesis. The polymer layers can be solidified before removal of the matrix or, in some embodiments, after the matrix is removed.

Pressing the stent into the polymer deforms the matrix and decreases the amount of exposed surface area on the stent. The more surface area exposed on the stent, the more difficult it is to completely cover the stent with a second layer of polymer. There is a higher likelihood of deformation if the stent is not substantially or completely covered.

The stent has a first side which contacts the first layer of polymer and a second side on the opposing side of the stent. In some embodiments, a second layer of polymer is applied over at least a portion of the stent and the first layer such that the second side of the stent is covered by the second layer of polymer. There are embodiments where the second layer is applied over the first layer of polymer while not contacting the first layer. There may be intervening layers of polymer or, in some embodiments, graft material between the first and second layers of polymer. The second layer of polymer is applied over at least a portion of the stent and first layer to the extent the first layer covers, whether in direct or indirect contact, the stent and first layer.

Figure 1B:
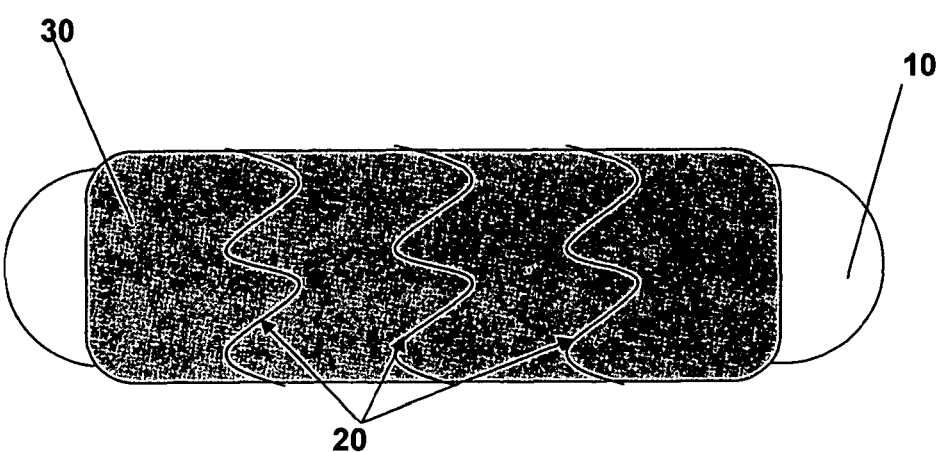
FIG. 1B illustrates stents placed over a layer of polymer and the mandrel.

The deformable matrix may be further deformed or shaped in some embodiments to provide a shaped endovascular prosthesis. The deformable matrix is removed upon curing without substantially disrupting the polymer covering. In embodiments that may be preferred, the endovascular prosthesis is a stent encased in polymer and the deformable matrix or substrate used to form the prosthesis is a mandrel. In the embodiment illustrated in FIG. 1A, the polymer 30 is layered onto the outer surface, or ablumen, of the mandrel. In other embodiments, the layer is sprayed or coated on the deformable matrix. The amount of polymer 30 applied to the deformable matrix varies according to manufacturing preferences. In some embodiments, a first layer of polymer 30 may be added to provide a thickness of about 0.08 mm to about 0.3 mm on the matrix and all combinations and subcombinations therein. As seen in FIG. 1B, three stents 20 are placed onto the polymer coated mandrel 10. In other embodiments, at least one stent 20 contacts the polymer. The number of stents 20 used is a matter of manufacturing preference. The deformable matrix can exhibit plasticity during application of the polymer layers and stent.

The stent 20 is pressed or crimped into the mandrel 10, reducing the exposed surface area of the stent 20. FIG. 2B illustrates a cross-sectional view of the mandrel embodiment in which the first layer of polymer 30 is also pressed into the outer surface of the mandrel 10 as a result of the stent 20 being pressed into the mandrel 10. The first side 22 of the stent 20 faces the mandrel 10. The stent 20 is pressed into the polymer 30 to varying depths depending on manufacturing technique. The stent 20 can be pressed into the polymer 30 toward the mandrel 10 to decrease the amount of exposed surface area to a point where only a portion of the second, or outer, side 24 of the stent 20 is exposed. In some embodiments, the stent 20 can be pressed into the polymer 30 to a depth nearly equal to the strut thickness of the stent 20. In other embodiments, the stent 20 is pressed into the mandrel 10 such that the second side 24 of the stent is substantially level with the first layer of polymer 30. In these cases, the outer diameter of the stent is then substantially the same as the outer diameter of the mandrel. In yet another embodiment, the stent 20 is pressed toward the mandrel 20 to any depth that decreases the amount of exposed surface area of the stent 20.

In some embodiments, the stent is not pressed into the deformable matrix. When a mandrel 10 is used as the deformable matrix, the stent 20 can be held fixed around the mandrel 10 and the diameter of the mandrel 10 is expanded to contact the stent 20. As will be explained below, where a mold is used as the deformable matrix, the stent can be placed along the mold's inner surface and pressed into the mold by using a balloon catheter.

A second layer 35 of polymer is applied onto the exposed second side 24 of the stent. The second layer 35 may contact the first layer 30 at certain portions not covered by the stent 20. There are embodiments where the second layer 35 of polymer is applied onto a portion of the deformable matrix, or mandrel 10, and the exposed surface area of the stent 20. In some embodiments, the second layer 35 of polymer covers the first layer 30 of polymer and stent 20. The amount of second layer 35 of polymer is also dependent on manufacturing preferences. In some embodiments, a second layer 35 of polymer may be added to provide a thickness of about 0.025 mm to about 0.100 mm and all combinations and subcombinations therein. In some embodiments, both layers of polymer cure to form one layer that encapsulates the stent 20. In some embodiments that may be preferred, the first layer 30 and the second layer 35 comprise identical polymer. There are also embodiments where polyurethane, such as Thoralon®, comprises the first layer and second layer of polymer.

Figure 2A:
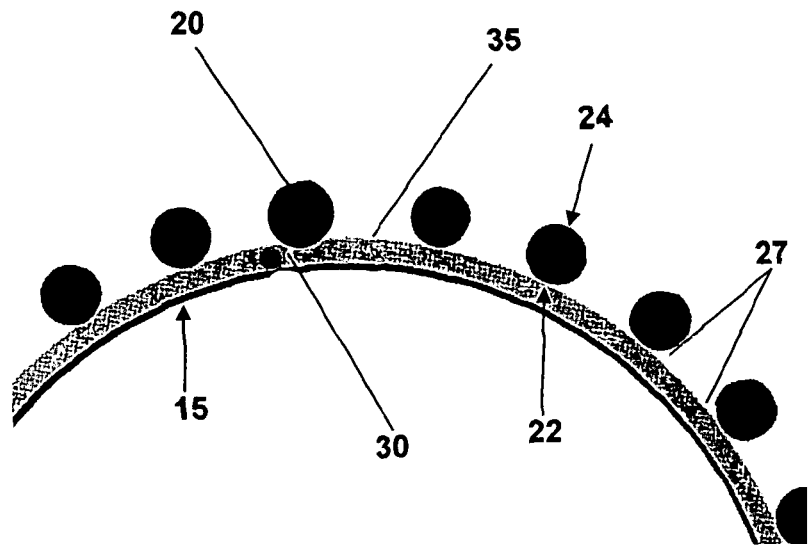
FIG. 2A is a schematic representation of a cross sectional view of an endovascular prosthesis made by the prior art covering technique.
Figure 2B:
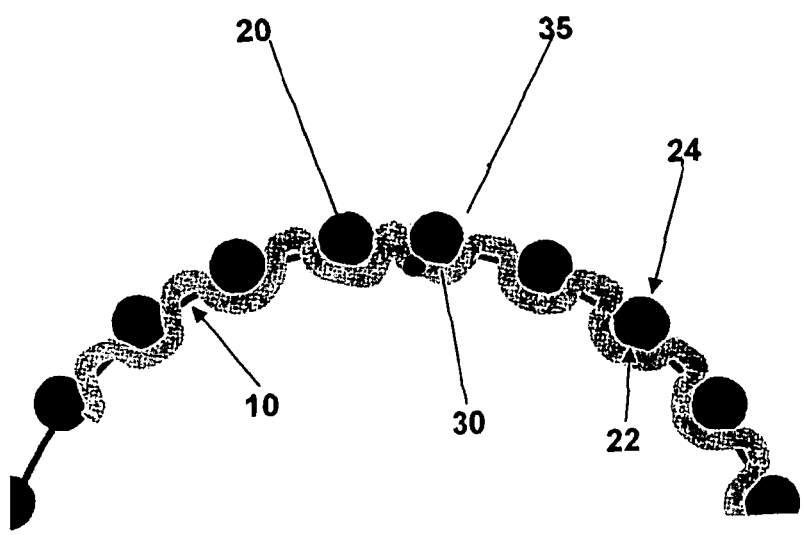
FIG. 2B schematically represents a cross sectional view of the endovascular prosthesis made by the covering technique of the present invention.

FIG. 2A shows a cross section of an endovascular prosthesis with a stent 20 made by a prior art covering technique. A first layer 30 of polymer is added onto a non-deformable, or glass, mandrel 15. A stent 20 is placed on top of the first layer 30 before a second layer 35 of polymer is applied. The second layer 35 does not cure uniformly around the stent. Gaps 27 can be seen on either side of the struts of the stents 20. In the present invention, as shown in FIG. 2B, the second layer 35 of polymer is applied onto a decreased surface area on the second side 24 of the stent 20 and is, therefore, capable of more uniform curing.

The first 30 or second 35 layer of polymer can be coated onto the deformable matrix by dipping, spraying, or casting. In other embodiments, the polymer can be applied by application with rollers or brushes. Some polymers used may shrink when cured and may be likely to cure towards a smaller surface area on the matrix 10. The polymer can be solidified by methods known in the art, such as curing, cooling, or chemical reaction.

Figure 3:
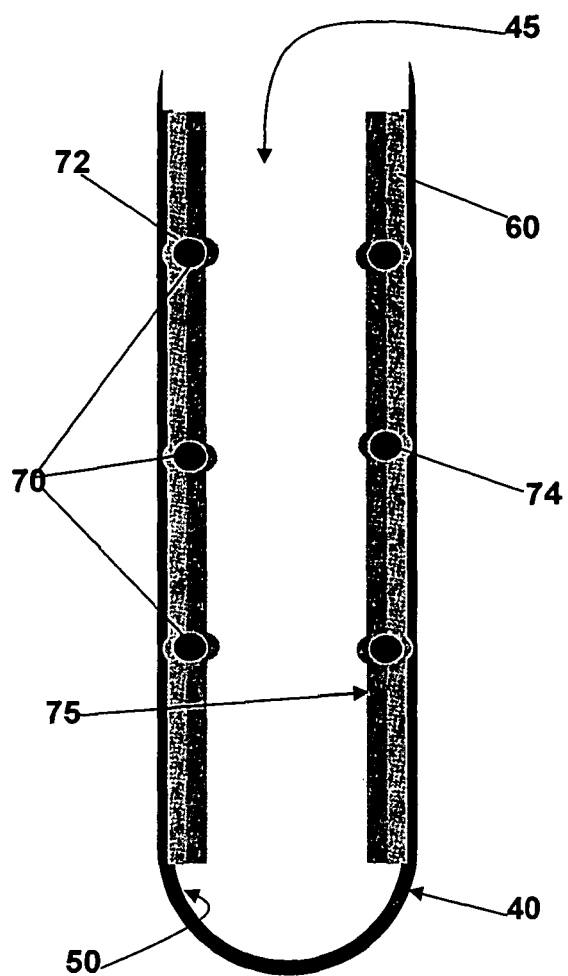
FIG. 3 illustrates a cross sectional view of stents obtruded into the inner surface of a hollow mandrel.

There are also embodiments where the deformable matrix is a mold. As seen in the embodiment shown in FIG. 3, the mold 40 has a lumen 45. FIG. 3 illustrates a cross-sectional area of the endovascular prosthesis being made using the methods of the present invention. The mold 40 has a lumen 45 and an inner surface 50. A first layer 60 of polymer is applied on a portion of the inner surface 50 of the mold 40. In some embodiments not illustrated, the inner surface 50 of the mold 40 is covered completely by the first layer 60 of polymer. In other embodiments, at least a portion of the inner surface 50 is covered by the first layer 60. A stent 70 is placed in the lumen 45 of the deformable mold 40 such that the first side 72 of the stent 70 faces the first layer 60 of polymer and the inner surface 50 of the mold 40. The stent 70 is then obtruded into the first layer 60 of polymer and also the inner surface 50 of the mold 40. The stent 70 may be obtruded by a balloon catheter (not shown), for example. A second layer 75 of polymer is coated over at least a portion of the stent 70 and first layer 60. In this embodiment, the second layer 75 is coated over the second, or outer, surface 74 of the stent 70. The second side 74 is the exposed surface area of the stent 70. In some embodiments, the second layer 75 of polymer will also be applied to a portion of the deformable matrix and exposed surface area of the stent 70. The first 60 and second 75 layers of polymer can be applied to the mold using techniques known in the art. In some embodiments that may be preferred, the first 60 and second 75 layers of polymer are solidified around the stent 70 to form the endovascular prosthesis before the mold is removed.

The deformable matrices of the present invention are preferably comprised of materials that are not significantly altered by the prosthesis making process. It is also preferable that the matrices are not comprised of materials that may bond to the polymer layers applied in the methods described herein. Preferably, the deformable matrices are made of a sacrificial material that is easily removed from contacting the formed endovascular prosthesis after curing.

The matrices of the present invention can undergo physical or chemical changes when removed from the formed endovascular prosthesis. In some embodiments, a wax matrix can be used. The matrix can be formed from a water soluble wax which is dissolvable in a dilute acid solution. The wax matrix can also be removed using solvents of high volatile organic content. In some embodiments, the matrix can be melted using heat. The matrix can also be comprised of elastomeric polymers, or polymers known to liquefy at high pressure. The elastomers can be any one of a number of compounded elastomers suitable for providing a deformable matrix. "Elastomer," as used herein, includes any polymer which exhibits flexibility in the temperature range of building and curing operations of the tubular products thereon and is capable of maintaining its shape.

Other embodiments of the present invention use deformable matrices that are removed by physical change. In addition to melting or evaporation, the matrix can be contracted, expanded, distended, compressed, or pulled away from the endovascular prosthesis. In embodiments where the matrix is a mandrel, the mandrel can be removed by diameter constriction. The constriction can be achieved by means known in the art as well as described herein.

Making endovascular prostheses using the methods described herein assists in better sizing of a stent with a mandrel. The deformable nature of the matrices of the current invention also provides more uniform coverage of the stent with polymer.

Figure 4A:
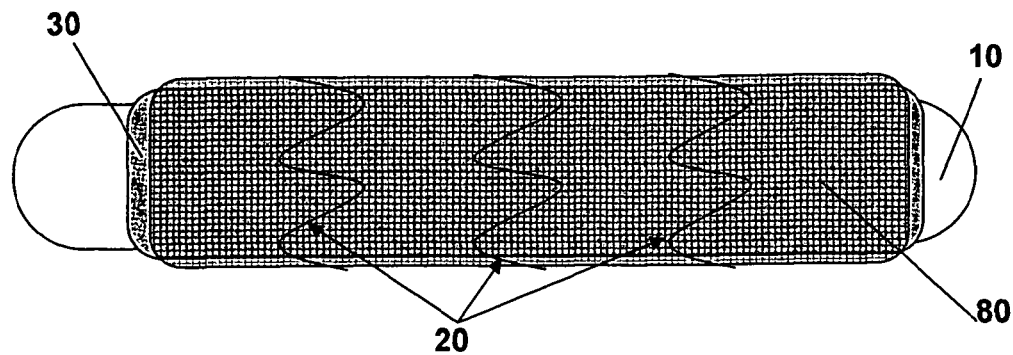
FIG. 4A is an exemplary illustration of a mandrel covered with polymer, graft material, and stents.
Figure 4B:
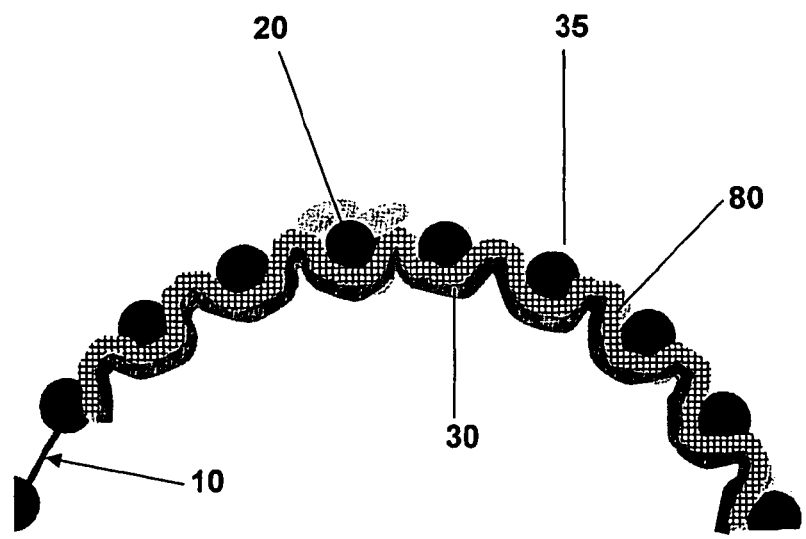
FIG. 4B illustrates a cross sectional view of the stent layered over the material and polymer on the mandrel.

The covering technique of the present invention can also be used to produce stent grafts. In some embodiments, the methods described above further comprise applying a graft material onto a portion of the deformable matrix. A stent is placed onto the graft material in some embodiments where a mandrel is used as the deformable matrix or along the graft material in embodiments using a mold as the deformable matrix. The stent is pressed into the deformable matrix and, as a result, portions of the graft material are also pressed into the deformable matrix. In some embodiments, the graft material is applied after the stent has been pressed into the deformable matrix. As seen in FIG. 4A, a stent 20 is placed over a graft material 80 that has been placed over polymer 30. FIG. 4B, is a cross sectional view of a stent graft where the first 30 layer of polymer, the graft material 80, and the stent 20 are pressed into a mandrel 10. In another embodiment that uses a mold as the deformable matrix, the graft material is applied over a portion of the inner surface of the mold. A stent is then pressed along with the graft material into the deformable mold. A second layer of polymer 35 is applied over at least a portion of the graft material 80 and stent 20. In some embodiments that may be preferred the polymer layers are then solidified.

The deformable matrix can be partially deformable or have a non-deformable core with a deformable, or sacrificial, surface layer. In such embodiments, the matrix can comprise a shape memory alloy core, such as nitinol, with a sacrificial covering. The deformable matrix can be deformed or further deformed by being bent, twisted, compressed, or manipulated into any 3D formation suitable for an endovascular prosthesis before the polymer layers are applied. The deformation may comprise longitudinal deformation instead of, or in addition to, radial deformation. In some methods of the present invention, the prosthesis is further manipulated after the polymer layers are applied but before curing or removal of the deformable matrix. The prosthesis can be shaped by mechanical means or non-mechanical means. A shaped endovascular prosthesis may exhibit anatomical advantages by being designed with a shape suitable for placement in a diseased vasculature such as an aortic arch or abdominal aorta.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A method of making an endovascular prosthesis having a desired shape comprising:
    applying a first layer of polymer onto a portion of a deformable forming member;
    contacting a stent with the polymer to deform the forming member;
    applying a second layer of polymer over at least a portion of the stent and first layer;
    solidifying the layers of polymer to form the endovascular prosthesis;
    removing the forming member; and
    wherein the deformable forming member exhibits plasticity during application of the polymer layers and stent.

2. The method of claim 1 further comprising pressing the stent into the deformable forming member.

3. The method of claim 1, wherein the deformable forming member comprises wax, polymer, elastomer, or shape memory alloy.

4. The method of claim 1, wherein the deformable forming member comprises a non-deformable core and a deformable surface.

5. The method of claim 1 wherein the deformable forming member is melted, dissolved, contracted, expanded, evaporated, or distended.

6. The method of claim 1, further comprising physically manipulating the endovascular prosthesis and deformable forming member to the desired shape before removing the deformable forming member.

7. The method of claim 1, further comprising pressing the stent toward the deformable forming member, physically manipulating the endovascular prosthesis and deformable forming member to the desired shape, and removing the deformable forming member.

8. The method of claim 1, wherein the first and second layers are solidified by cooling, curing, or chemical reaction.

9. A method of making an endovascular prosthesis having a desired shape comprising:
    applying a first layer of polymer to a portion of a deformable forming member;

applying a graft material over at least a portion of the first layer and deformable forming member;

contacting a stent with the graft material, to deform the forming member;

applying a second layer of polymer over at least a portion of the stent and graft material;

solidifying the layers of polymer to thereby form the endovascular prosthesis;

removing the forming member; and wherein the deformable forming member exhibits plasticity during application of the polymer layers and stent.

10. The method of claim 9 further comprising pressing the stent toward the deformable forming member.

11. The method of claim 9, wherein the deformable forming member comprises wax, polymer, elastomer, or shape memory alloy.

12. The method of claim 9, wherein the deformable forming member comprises a non-deformable core and a deformable surface layer.

13. The method of claim 9, wherein the deformable forming member is removed by undergoing a change.

14. The method of claim 13 wherein the deformable forming member is melted, dissolved, contracted, expanded, evaporated, or distended.

15. The method of claim 9, further comprising physically manipulating the stent and deformable forming member to the desired shape before removing the deformable forming member.

16. The method of claim 9, further comprising pressing the stent toward the deformable forming member, physically manipulating the endovascular prosthesis and deformable forming member to the desired shape, and removing the deformable forming member.

17. The method of claim 9, wherein the first and second layers are solidified by cooling, curing, or chemical reaction.

* * * * *

UNITED STATES PATENT AND TRADEMARK OFFICE
CERTIFICATE OF CORRECTION

PATENT NO. : 8,617,448 B2  Page 1 of 1
APPLICATION NO. : 12/598249
DATED : December 31, 2013
INVENTOR(S) : Jichao Sun It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 957 days.

Signed and Sealed this
Twenty-second Day of September, 2015

Michelle K. Lee
*Director of the United States Patent and Trademark Office*